(12) United States Patent
Shalaby et al.

(10) Patent No.: US 8,481,074 B2
(45) Date of Patent: Jul. 9, 2013

(54) HEMOSTATIC MICROFIBROUS CONSTRUCTS

(75) Inventors: Shalaby W. Shalaby, Anderson, SC (US); M. Scott Taylor, Pendleton, SC (US)

(73) Assignee: Poly-Med, Inc., Anderson, SC (US)

( * ) Notice: Subject to any disclaimer, the term of this patent is extended or adjusted under 35 U.S.C. 154(b) by 1248 days.

(21) Appl. No.: 11/175,635

(22) Filed: Jul. 5, 2005

(65) Prior Publication Data

US 2006/0013863 A1    Jan. 19, 2006

Related U.S. Application Data

(60) Provisional application No. 60/588,501, filed on Jul. 16, 2004.

(51) Int. Cl.
*A61F 13/00* (2006.01)
*C08L 31/00* (2006.01)
*C08G 65/34* (2006.01)

(52) U.S. Cl.
USPC .................. 424/443; 524/556; 528/425

(58) Field of Classification Search
None
See application file for complete search history.

(56) References Cited

U.S. PATENT DOCUMENTS

| | | | |
|---|---|---|---|
| 4,047,533 A * | 9/1977 | Perciaccante et al. | 606/230 |
| 5,578,046 A * | 11/1996 | Liu et al. | 606/151 |
| 5,593,778 A * | 1/1997 | Kondo et al. | 428/373 |
| 5,679,372 A | 10/1997 | Shimuzu et al. | |
| 6,033,719 A * | 3/2000 | Keogh | 427/2.12 |
| 6,162,537 A * | 12/2000 | Martin et al. | 428/373 |
| 6,511,748 B1 * | 1/2003 | Barrows | 428/373 |
| 6,528,107 B2 * | 3/2003 | Chinn et al. | 427/2.24 |
| 6,576,576 B1 * | 6/2003 | Wang et al. | 442/362 |
| 6,579,814 B1 * | 6/2003 | Lindquist et al. | 442/347 |
| 6,685,956 B2 | 2/2004 | Chu et al. | |
| 6,689,166 B2 | 2/2004 | Laurencin et al. | |
| 6,706,051 B2 | 3/2004 | Hudson et al. | |
| 2002/0119179 A1 * | 8/2002 | Rezania et al. | 424/426 |
| 2002/0161168 A1 * | 10/2002 | Shalaby et al. | 528/310 |
| 2002/0164365 A1 * | 11/2002 | Shalaby et al. | 424/426 |
| 2002/0168912 A1 * | 11/2002 | Bond et al. | 442/415 |
| 2003/0069369 A1 | 4/2003 | Belenkaya et al. | |
| 2003/0134099 A1 | 7/2003 | Barrows | |

OTHER PUBLICATIONS

Pendant Group, FreeDictionary pp. 1-3, accessed Feb. 2, 2010.*
J. Cardiovascular Surgery, 18, 486-493, (2003).
Polymer Preprints, 44(2), 82-83, (2003).

* cited by examiner

*Primary Examiner* — Scott Long
*Assistant Examiner* — Lyndsey Beckhardt
(74) *Attorney, Agent, or Firm* — McCormick, Paulding & Huber LLP

(57) ABSTRACT

Elastomeric fibrous constructs are formed from multicomponent, non-woven nano-/microfibers having a core and sheath configuration made primarily of an absorbable polymer and preferably a water-soluble one, respectively. Most preferably, the nano-/microfibers are produced by electrostatic spinning. Depending on clinical use of these constructs, suitable bioactive agents can be incorporated into the construct.

9 Claims, No Drawings

HEMOSTATIC MICROFIBROUS CONSTRUCTS

The present application claims the benefit of prior provisional application, U.S. Ser. No. 60/588,501, filed Jul. 16, 2004.

BACKGROUND OF THE INVENTION

It has been well established that fibrous constructs, as in the cellulose-based cotton gauzes, can aid the process of hemostasis through interrupting the blood flow and subsequent coagulation. Positively charged cellulosic fibers, such as those based on chitosan, were later recognized as effective hemostatic constructs. More recent understanding of the relevance of hemostasis to key biological events associated with wound healing, tissue ingrowth about prosthetic devices, and tissue engineering justified the need to explore means to modulating the hemostatic process to meet the specific requirements at different biological sites for optimum hemostasis and, hence, optimum functional performance at said sites. And this invention deals with mechanical, physicochemical, biochemical and pharmacological means to modulate the hemostatic process to meet the needs of specific individual biological events. To explore these means, this invention relies on (1) electrostatic spinning technology to produce nanometer and micrometer diameter fibers with exceptionally high surface area for maximized effect on blood flow to initiate the clotting cascade through contact activation; (2) producing inherently compliant and elastic components of the fibrous construct through the use of segmented crystalline copolymers having triaxial or polyaxial chain configuration (i.e., three or many chain branches extending outward from a central atom); (3) controlling the composition of electrostatically spun fiber precursors to provide constructs with controlled solubility and biodegradability and hence, modulated short- and long-term retention of mass and biologically relevant properties; (4) controlling the surface charge of the electrostatically spun fibers to physicochemically modulate the hemostasis at will; and (5) incorporating judiciously bioactive agents to prevent infection, pain, and/or promote desirable biological events.

The topic of hemostasis and commercially available hemostatic sealants and their mechanisms of action have been treated in a recent review [*J. Cardiovascular Surgery*, 18, 486 (2003)]. It was noted in this review that application of direct pressure at a bleeding site frequently provides either complete control of bleeding or adequate control to enable more definitive measures to be taken. However, this method of controlling bleeding may not be sufficient when the source of bleeding is hard to identify, as may be the case for diffuse venous bleeding, or when an inherent coagulopathy is present. Intraoperative coagulopathy, which can be induced by a variety of factors including hemodilution and hypothermia, may be treated with active hemostatic agents. Hemostasis is also compromised due to the presence of antiplatelet and anticoagulation agents, especially in patients undergoing cardiac or vascular surgery, as well as from changes associated with cardiopulmonary bypass. In such cases, topical hemostatic agents become useful adjuncts to the conventional methods of achieving hemostasis. A comprehensive list of currently available topical hemostatic agents, together with their key attributes, is presented in Table I.

TABLE I

Comparison of Topical Hemostatic Agents

| Commercial Material | Mechanism of Action | What It Needs to Work |
|---|---|---|
| Cellulose | | |
| Surgicel Oxycel | Cellulose fibers initiate clotting cascade through contact activation | Functional clotting cascade and all clotting factors |
| Gelatin | | |
| Gelfoam Sponge Powder Film Surgifoam | Initiation of clotting cascade through contact activation | Functional clotting cascade and all clotting factors |
| Collagen | | |
| Avitene Flour Sheet | Contact activation and promotion of platelet aggregation to initiate the clotting cascade | Functional clotting cascade and all clotting factors |
| Actifoam Sponge Instat (flour) Helistat/ Helitene | Contact activation and promotion of platelet aggregation to initiate the clotting cascade | Functional clotting cascade and all clotting factors. |
| Floseal Matrix Hemostatic Sealant | Gelation granules restrict the flow of blood, provide a physical matrix around which a clot can form, and deliver and maintain thrombin to the tissue surface | Circulating fibrinogen |
| Thrombin | | |
| Thrombin JMI | Interacts with fibrinogen in the patient's blood to form a fibrin clot | Circulating fibrinogen and a means of delivery (customarily used with Gelfoam sponges or powder) for use on active bleeding |
| Fibrin Glue | | |
| Tisseel Hemaseel Fibrin Glue Variants Costasis Dynastat | Mixes fibrinogen, thrombin and factor XIII dispensed from a double barrel syringe to generate a clot. Fibrin glue also includes aprotinin (bovine-derived) to prevent fibrinolysis. CoStasis/Dynastat include collagen, but not aprotinin | Fibrin glue must be warmed prior to use (20-to-40 minute process) CoStasis/Dynastat requires patient's blood to be drawn and centrifuged Can only apply to a dry, stationary tissue surface |
| Aldehyde Glues | | |
| Bioglue | Glutaraldehyde and albumin cross-linked with proteins in tissue forming a strong adhesive | Dry thoracic aortic tissue Tissue that can withstand exogenous cross-linking |

The term hemostatic agent (or material) has been defined (U.S. Pat. No. 6,706,051) as any agent or material that is capable of arresting, stemming, or preventing bleeding by means other than inducing tissue growth alone. In other words, something other than tissue growth is at least partially responsible for retarding or preventing bleeding. Preferably, the agent or material will be one that enhances blot clot formation. It will, of course, be appreciated that the agent or material may have the beneficial property of inducing tissue growth in addition to retarding or preventing bleeding. Examples of preferred hemostatic agents which enhance blood coagulation include carboxymethylcellulose (CMC), oxidized cellulose, calcium alginate, gelatin, or collagen, oxidized cellulose, such as Tabotamp™, is another example of a hemostatic agent. Falling under the definition of "hemostatic agent" is the cellulose-based cotton gauze, the first and gold standard for all-time surgeons. The early successful application of the cotton gauze as a hemostatic construct led several investigators to associate the fibrous structure of the gauze with the interruption of blood flow by initiating the clotting cascade through contact activation. This, in turn, provided the incentive to examine other fibrous constructs made primarily from natural materials, such as collagen, chitosan, and alginate, which led subsequently to the discovery of surface charge contribution to hemostasis. With the development of synthetic absorbable/biodegradable fibers, several investigators directed their attention to fibrous synthetic polyester as transient alternatives or additives to more traditional natural fibers used in earlier hemostatic constructs. Illustrations of such typical disclosures are summarized below.

EP Application No. 99933226.5 described a local absorbent hemostatic material coating the surface of fibers composed of material having biocompatibility and which can be degraded and absorbed in the living body, with extracted collagen. The hemostatic material having biocompatibility and which can be degraded and absorbed in the living body was selected from the group consisting of polyglycolic acid, polylactic acid, copolymer of glycolic acid and lactic acid, polydioxanone, copolymer of glycolic acid and trimethylene carbonate, mixtures of polyglycolic acid and polylactic acid, and oxycellulose.

U.S. Pat. No. 5,679,372 described an absorbable spun, cotton-like topical hemostat containing fibers entangled with each other and being made of atelcollagen obtained by reconstituting solubilized collagen. Each of the fibers has a diameter of 10 to 70 µM and a length of 3 to 70 mm. At least a part of the collagen molecules constituting the fibers are crosslinked by heat at a temperature of 50° to 200° C. The hemostat is swellable upon contact with blood. In use, the hemostat readily adapts to the shape of the hemorrhagic site, has an adhesiveness to a bleeding surface and provides an effective suppression of hemorrhage.

Growing interest in absorbable polymers in the form of scaffolds for tissue engineering has revived interest in electrospinning of synthetic polymers and, in particular, absorbable ones to produce nanofibers and microfibers with exceptionally high surface area. And a logical extension of this integrated know-how was the development of absorbable nanofibers and microfibers for use in hemostatic constructs. An outline of a generic electrospinning process and illustrations of key developments are summarized below.

Electrostatic spinning (or simply electrospinning, ES) is the manufacturing technique most often associated with the production of polymeric nanofibers. In this technique, a polymer is dissolved in a solvent or melted and placed in a glass pipette tube, sealed at one end with a small opening in a necked down portion at the other end. A high voltage potential up to 50 kv is then applied between the polymer solution and a collector near the open end of the pipette. This process can produce nanofibers with diameters as low as 50 nanometers, although the collected web usually contains fibers with varying diameters from 30 nm to over one micron. The production rate of this process is often measured in grams per hour per spin hole or nozzle, and the fiber strength (grams/denier) is thought to be very low, but is difficult to measure.

For tissue engineering, it has been recognized that components of biocompatible scaffolds or matrices or nanometer or micrometer diameter fibers provide favorable environments for cell adhesion, cell proliferation, and directed cellular growth. Fibrous and fibrillar organic and inorganic materials of nanometer or micrometer diameter can be constructed into non-woven, three-dimensional matrices conducive to cell seeding and proliferation. These three-dimensional scaffolds or matrices can then be fabricated into appropriate shapes to stimulate hierarchical micro- and macro-geometry of tissue and or organs to be repaired or replaced. Accordingly, the inventor of U.S. Pat. No. 6,689,166 argued that with new developments in wound healing and tissue engineering, it would be of great advantage to substitute absorbable/biodegradable constructs that are commonly used in medical applications comprised mostly of fibers having diameters that exceed 10 µM with those made of electrospun fibers having smaller diameters. Examples of these applications can include surgical reconstruction and tissue replacement procedures associated with trauma, pathological degradation, or congenital deformity of tissues. Reconstructive surgery is based upon the principle of replacing defective tissues with viable, functioning alternatives. In skeletal applications, surgeons have historically used bone grafts. The two main types of bone grafts currently used are autografts and allografts. Both types of bone grafts have several limitations and synthetic alternatives will be most desirable. U.S. Pat. No. 6,689,166 also describes a tissue engineering device comprising a matrix of biocompatible non-woven nanofibrils comprising a non-degradable polymer selected from the group consisting of polyethylenes and polyurethanes or a degradable polymer selected from the group consisting of poly(lactic acid-glycolic acid), and poly(lactic acid), poly(glycolic acid), poly(glaxanone), poly(orthoesters), poly(pyrolic acid), and poly(phosphazenes). It was further disclosed that the tissue engineering devices comprise absorbable organic polymers in the form of nanometer fibers that are produced by electrostatic spinning and an inorganic component made of calcium phosphate-based ceramic material.

U.S. Pat. No. 6,685,956 described biodegradable and/or bioabsorbable fibrous articles and methods for using the articles in medical applications. The biodegradable and/or bioabsorbable fibrous articles, which are formed by electrospinning fibers of biodegradable and/or bioabsorbable fiberizable material, comprise a composite (or asymmetric composite) of different biodegradable and/or bioabsorbable fibers. The patent further discloses (1) that the biodegradable and/or bioabsorbable fibrous articles are formed by electrospinning fibers of biodegradable and/or bioabsorbable fiberizable material, in which the article contains a composite of different biodegradable and/or bioabsorbable fibers; (2) that preferably, the biodegradable and/or bioabsorbable fiberizable material is a biodegradable and/or bioabsorbable polymer—the biodegradable and/or bioabsorbable polymer preferably contains a monomer selected from the group consisting of a glycolide, lactide, dioxanone, caprolactone, trimethylene carbonate, ethylene glycol, and lysine; and (3) that fibrous articles formed by electrospinning different fibers of different materials, in which the article contains a composite of different fibers containing fibers of at least one biodegradable material and fibers of at least one non-biodegradable material (preferably, the compositite of different fibers contains submicron diameter fibers—the composite can be an asymmetric composite).

Electrospinning is a useful process to produce polymeric fibers in the average diameter range of 100 nm to about 5 µM, which is associated with a number of attributes. These fibers (1) possess a high aspect ratio that leads to a large specific surface; and (2) have been suggested to find applications ranging from optical and chemo sensor materials, nanocomposite materials, nanofibers with specific surface chemistry to tissue scaffolds, wound dressings, drug delivery systems, filtration, and protective clothing. The effects of several process parameters, such as the applied electric field strength, flow rate, concentration, distance between the capillary and the target, have been explored in great detail for different polymer materials. Most of the systems that have been investigated to date have utilized electrospinning from a single solution or melt. Going further beyond single nanofiber and microfiber constructs, a new direction of nano-/microfibrous blends has been pursued by a number of investigators and inventors. In a successful attempt to produce nanofiber/microfiber composites with two distinctly separated fibers, a number of investigators [*Polymer Preprints*, 44(2), 82 (2003)] were able to design an electrospinning device where two polymer solutions have been electrospun simultaneously in a side-by-side fashion. This allows having a bicomponent system that will have properties from each of the polymeric components, e.g., one of the polymers could contribute to the mechanical strength while the other could enhance the wettability of the resulting non-woven web. The wettability of the electrospun mat can also be controlled by varying its porosity. By a systematic change of one of the process parameters (say the distance between the capillary-end and the grounded target or the flow rate), while keeping the other constant, the porosity of the electrospun mat can be altered. This study also described a new bicomponent electrospinning device and presented results of poly(vinyl chloride)/segmented polyurethane (PVC/Estane) and poly(vinyl chloride)/poly(vinylidiene fluoride) ((PVC/PVDF) bicomponent fibers.

Meanwhile, U.S. application Ser. No. 10/267,823 described medical constructs made of microfibrous blends of absorbable and water-soluble polymers. And this application deals with a biodegradable, absorbent microfiber comprising a substantially homogeneous mixture of at least one hydrophilic polymer and at least one biodegradable polymer. The absorbent fibers can be prepared by an electro hydrodynamic spinning of a substantially homogeneous polymer mixture and used as medical dressing for burns and wounds, cavity dressings, drug delivery patches, face masks, implants, drug carriers that comprise at least one microfiber electrospun from a polymer mixture. The dressings can have variable water vapor penetration characteristics and variable biodegradation times. Some embodiments of the invention provide dressings, implants, dermatological compatible compositions and drug carrier compositions which include totally biodegradable non-gel materials having water, blood, and other biological liquids absorption ability and possessing biological active properties like haemostatic and wound healing acceleration ability, which are irreversible, retain their contour and shape when wet, and do not exhibit any swelling. Additional embodiments provide totally biodegradable microfiber absorbents on the base of blends of synthetic biodegradable polyesters and poly(N-vinyl) lactams. These materials can be used in a variety of products such as cavity dressings, drug delivery patches, face masks, implants, drug carriers, wound and burn dressings with predicable biodegradation times and controlled absorption of biological liquids including blood, and with variable vapor penetration and controlled drug release for wounds and burns.

Although the prior art discussed in the preceding paragraphs deals with several aspects of hemostasis and means to achieve it, including the use of non-woven compositions made of nano/microfibers, it fails to describe novel means or compositions needed to modulate the hemostatic process at different biological sites with different requirements for optimum hemostasis that insures maximized functional performance. This provided the incentive to explore the subject of this invention. Accordingly, this invention deals with (1) the technology of electrostatic spinning to produce nanometer and micrometer diameter fibers with exceptionally high surface area for maximized effect on blood flow to initiate the clotting cascade through contact activation; (2) produce inherently compliant and elastic components of the fibrous construct through the use of segmented crystalline copolymers having triaxial or polyaxial chain configuration (i.e., three or many chain branches extending outward from a central atom); (3) controlling the composition of electrostatically spun fiber precursors to provide constructs with controlled solubility and biodegradability and hence, modulated short- and long-term retention of mass and biologically relevant properties; (4) controlling the surface charge of the electrostatically spun fibers to physicochemically modulate the hemostasis at will; and (5) judicious incorporation of bioactive agents to prevent infection, pain, and/or promote desirable biological events.

SUMMARY OF THE INVENTION

This invention deals in general with a hemostatic, compliant, elastomeric, multicomponent, fibrous construct comprising non-woven nanometer and micrometer diameter fibers made from at least one polymer selected from the groups represented by synthetic absorbable/biodegradable heterochain polymers, synthetic water-soluble heterochain polymers, synthetic water-soluble homochain polymers, and polysaccharides or derivatives thereof. Another general aspect of this invention deals with a hemostatic, compliant, elastomeric, fibrous construct comprising a non-woven material comprising fibers having a diameter in the range of from about 50 nm to about 10 µm, the fibers having a core/sheath configuration and made from a synthetic absorbable/biodegradable polymer and at least one further polymer selected from a synthetic water-soluble polymer and another synthetic absorbable/biodegradable polymer.

A specific aspect of this invention deals with a hemostatic, compliant, elastomeric, multicomponent, fibrous construct comprising non-woven nanometer and micrometer diameter fibers made from at least one polymer selected from the groups represented by synthetic absorbable/biodegradable heterochain polymers, synthetic water-soluble heterochain polymers, synthetic water-soluble homochain polymers, and polysaccharides or derivatives thereof, wherein the nanometer and micrometer diameter fibers are produced by electrostatic spinning of a solution of at least one absorbable polymer made from at least one monomer selected from the group represented by ε-caprolactone, dl-lactide, 1-lactide, glycolide, trimethylene carbonate, 1,5-dioxepan-2-one, p-dioxanone, and a substituted or unsubstituted morpholine-2-5-dione.

Another specific aspect of this invention deals with a hemostatic, compliant, elastomeric, multicomponent, fibrous construct comprising non-woven nanometer and micrometer diameter fibers made from at least one polymer selected from the groups represented by synthetic absorbable/biodegradable heterochain polymers, synthetic water-soluble heterochain polymers, synthetic water-soluble homochain polymers, and polysaccharides or derivatives thereof, wherein the nanometer and micrometer diameter fibers are produced by electrostatic spinning of a solution comprising an absorbable/biodegradable polymer made from at least one monomer selected from the group represented by ε-caprolactone, dl-lactide, 1-lactide, glycolide, trimethylene carbonate, 1,5-dioxepan-2-one, p-dioxanone, a substituted or unsubstituted morpholine-2-5-dione, and a synthetic, water-soluble polymer selected from the group represented by polyethylene oxide, polyethylene glycol, block copolymer of ethylene and propylene glycol, polyhydroxyethyl methacrylate, poly-N-vinyl pyrrolidone and polyethylene glycol interlinked by an ester or urethane-containing interlink, wherein the absorbable/biodegradable and water-soluble constituents of the spinning solution result in biocomponent fibers having a core and sheath component derived primarily from the absorbable/biodegradable and water-soluble polymer, respectively, and preferably the water-soluble polymer is polyethylene glycol and the absorbable/biodegradable polymer is a triaxial segmented copolyester based on at least two monomers selected from the group represented by $\epsilon$-caprolactone, dl-lactide, l-lactide, glycolide, trimethylene carbonate, 1,5-dioxepan-2-one, p-dioxanone, and a substituted or unsubstituted morpholine-2-5-dione.

Another specific aspect of this invention deals with a hemostatic, compliant, elastomeric, multicomponent, fibrous construct comprising non-woven nanometer and micrometer diameter fibers made from at least one polymer selected from the groups represented by synthetic absorbable/biodegradable heterochain polymers, synthetic water-soluble heterochain polymers, synthetic water-soluble homochain polymers, and polysaccharides or derivatives thereof, wherein the nanometer and micrometer diameter fibers are produced by electrostatic spinning of a solution comprising an absorbable/biodegradable polymer made from at least one monomer selected from the group represented by $\epsilon$-caprolactone, dl-lactide, 1-lactide, glycolide, trimethylene carbonate, 1,5-dioxepan-2-one, p-dioxanone, a substituted or unsubstituted morpholine-2-5-dione, and a synthetic, water-soluble polymer selected from the group represented by polyethylene oxide, polyethylene glycol, block copolymer of ethylene and propylene glycol, polyhydroxyethyl methacrylate, poly-N-vinyl pyrrolidone and polyethylene glycol interlinked by an ester or urethane-containing interlink, and wherein the absorbable/biodegradable and water-soluble constituents of the spinning solution result in bicomponent fibers having a core and sheath component derived primarily from the water-soluble and absorbable/biodegradable polymer, respectively.

Another aspect of the invention pertains to hemostatic, compliant, elastomeric, multicomponent, fibrous construct comprising non-woven nanometer and micrometer diameter fibers made from at least one polymer selected from the groups represented by synthetic absorbable/biodegradable heterochain polymers, synthetic water-soluble heterochain polymers, synthetic water-soluble homochain polymers, and polysaccharides or derivatives thereof, wherein the nanometer and micrometer diameter fibers are produced by electrostatic spinning of a solution comprising an absorbable/biodegradable polymer made from at least one monomer selected from the group represented by $\epsilon$-caprolactone, dl-lactide, 1-lactide, glycolide, trimethylene carbonate, 1,5-dioxepan-2-one, p-dioxanone, a substituted or unsubstituted morpholine-2-5-dione, and a synthetic, water-soluble polymer selected from the group represented by polyethylene oxide, polyethylene glycol, block copolymer of ethylene and propylene glycol, polyhydroxyethyl methacrylate, poly-N-vinyl pyrrolidone and polyethylene glycol interlinked by an ester or urethane-containing interlink, wherein the absorbable/biodegradable and water-soluble constituents of the spinning solution result in bicomponent fibers having a core and sheath component derived primarily from the absorbable/biodegradable and water-soluble polymer, respectively, and preferably the water-soluble polymer is a poly-N-vinyl pyrrolidone and the absorbable/biodegradable polymer is a triaxial segmented copolyester based on at least two monomers selected from the group represented by $\epsilon$-caprolactone, dl-lactide, 1-lactide, glycolide, trimethylene carbonate, 1,5-dioxepan-2-one, p-dioxanone, and a substituted or unsubstituted morpholine-2-5-dione.

In yet another aspect the present invention is directed to a hemostatic, compliant, elastomeric, fibrous construct as set forth in claim 3 wherein the water-soluble polymer is selected from the group consisting of polyethylene oxide, polyethylene glycol, and a block copolymer of ethylene and propylene glycols, and wherein the absorbable/biodegradable polymer further comprises pendant carboxyl groups ionically conjugated with a basic compound selected from the group consisting of lysine, arginine, a basic oligopeptide, antiseptic agents, anesthetic agents, analgesic agents, antimicrobial agents, anti-inflammatory agents, antiviral agents and growth promoters.

Another aspect of this invention deals with use of said fibrous construct, the subject of this invention as (1) a lint-free, absorbent surgical pad; (2) an adjuvant in surgical procedures selected from the group represented by vascular anastomosis with sutures or tissue adhesives, intestinal anastomosis with sutures, staples or tissue adhesives, vascular repair entailing synthetic vascular graft using sutures or tissue adhesives, and structural repair of a biological conduit entailing synthetic prosthesis using sutures, staples, or tissue adhesives; and (3) a pledget for repairing soft tissue as in liver, kidney, pancreas, and lung using sutures, clips, or tissue adhesives. It is preferred that those constructs comprise a bioactive agent selected from the group represented by antimicrobials, antiseptics, anesthetics, analgesics, wound healing agents, anti-inflammatory compounds, antiviral agents and growth promoters.

A key aspect of the invention deals with a fibrous construct, subject of this invention, as a cover of a prosthetic device to aid/promote tissue ingrowth and mechanical stabilization of said prosthesis, wherein the prosthesis is selected from the group represented by endovascular grafts, perivascular wraps, vascular patches, endovascular stents, and similar stents for repairing biological conduits or restoring their function, endosteal implants, orthopedic implants, and implants for soft and hard tissue engineering. It is preferred that those constructs comprise a bioactive agent selected from the group represented by antimicrobials, antiseptics, anesthetics, analgesics, wound healing agents, anti-inflammatory compounds, antiviral agents and growth promoters.

Another key aspect of this invention pertains to a hemostatic, compliant, elastomeric, multicomponent, fibrous construct comprising non-woven nanometer and micrometer diameter fibers made from at least one polymer selected from the groups represented by synthetic absorbable/biodegradable heterochain polymers, synthetic water-soluble heterochain polymers, synthetic water-soluble homochain polymers, and polysaccharides or derivatives thereof, wherein said construct comprises a bioactive agent selected from the group represented by antimicrobials, antiseptics, anesthetics, analgesics, wound healing, anti-inflammatory, growth promoters, and antiviral agents.

A specific aspect of this invention deals with a hemostatic, compliant, elastomeric, multicomponent, fibrous construct comprising non-woven nanometer and micrometer diameter fibers made from at least one polymer selected from the groups represented by synthetic absorbable/biodegradable heterochain polymers, synthetic water-soluble heterochain polymers, synthetic water-soluble homochain polymers, and polysaccharides or derivatives thereof, wherein the nanometer and micrometer diameter fibers are produced by electrostatic spinning of a solution comprising an absorbable/biodegradable polymer made from at least one monomer selected from the group represented by ε-caprolactone, dl-lactide, 1-lactide, glycolide, trimethylene carbonate, 1,5-dioxepan-2-one, p-dioxanone, a substituted or unsubstituted morpholine-2-5-dione, and a synthetic, water-soluble polymer selected from the group represented by polyethylene oxide, polyethylene glycol, block copolymer of ethylene and propylene glycol, polyhydroxyethyl methacrylate, poly-N-vinyl pyrrolidone and polyethylene glycol interlinked by an ester or urethane-containing interlink, and preferably the water-soluble component is a polyvinyl pyrrolidone complexed with iodine.

Another specific aspect of the invention pertains to a hemostatic, compliant, elastomeric, multicomponent, fibrous construct comprising non-woven nanometer and micrometer diameter fibers made from at least one polymer selected from the groups represented by synthetic absorbable/biodegradable heterochain polymers, synthetic water-soluble heterochain polymers, synthetic water-soluble homochain polymers, and polysaccharides or derivatives thereof, wherein the nanometer and micrometer diameter fibers are produced by electrostatic spinning of a solution comprising an absorbable/biodegradable polymer made from at least one monomer selected from the group represented by ε-caprolactone, dl-lactide, 1-lactide, glycolide, trimethylene carbonate, 1,5-dioxepan-2-one, p-dioxanone, a substituted or unsubstituted morpholine-2-5-dione, and a synthetic, water-soluble polymer selected from the group represented by polyethylene oxide, polyethylene glycol, block copolymer of ethylene and propylene glycol, polyhydroxyethyl methacrylate, poly-N-vinyl pyrrolidone and polyethylene glycol interlinked by an ester or urethane-containing interlink, and preferably the water-soluble component is polyethylene glycol or block copolymer of ethylene and propylene glycol comprising a conjugate of carboxyl-bearing absorbable copolyester and a basic compound selected from the group represented by lysine, arginine, a basic oligopeptide, antiseptic agents, anesthetic agents, analgesic agents, antimicrobial agents, anti-inflammatory agents, antiviral agents and growth promoters.

An important aspect of this invention deals with a hemostatic, compliant, elastomeric, multicomponent, fibrous construct comprising non-woven nanometer and micrometer diameter fibers made from at least one polymer selected from the groups represented by synthetic absorbable/biodegradable heterochain polymers, synthetic water-soluble heterochain polymers, synthetic water-soluble homochain polymers, and polysaccharides or derivatives thereof, wherein the nanometer and micrometer fibers are produced by electrostatic spinning of a solution of at least one polymer that absorbs in less than 120 days and at least one additional polymer that absorbs after more than 120 days wherein each of these polymers is made from at lest one monomer selected for the group represented by ε-caprolactone, dl-lactide, 1-lactide, glycolide, trimethylene carbonate, 1,5-dioxepan-2-one, p-dioxanone, and a substituted or unsubstituted morpholine-2-5-dione, and preferably at least one of the polymers comprises a linear chain absorbable copolyester and an additional polymer comprising an absorbable copolyester comprising polyaxial copolyester chains.

A key segment of this invention pertains to a hemostatic, compliant, elastomeric, multicomponent, fibrous construct comprising non-woven nanometer and micrometer diameter fibers made from at least one polymer selected from the groups represented by synthetic absorbable/biodegradable heterochain polymers, synthetic water-soluble heterochain polymers, synthetic water-soluble homochain polymers, and polysaccharides or derivatives thereof, wherein the nanometer and micrometer diameter fibers are produced by electrostatic spinning of a solution of at least one absorbable polymer made from at least one monomer selected from the group represented by ε-caprolactone, dl-lactide, 1-lactide, glycolide, trimethylene carbonate, 1,5-dioxepan-2-one, p-dioxanone, and a substituted or unsubstituted morpholine-2-5-dione, wherein such construct is part of the external wall of a vascular graft having a surface-activated, non-absorbable lumen comprising knitted or woven monofilament or multifilament yarn made of at least one polymer selected from the group represented by polyethylene, polypropylene, poly(ethylene-co-polypropylene, polyether-ether ketone, polyethylene terephthalate, poly(ethylene-co-tetrafluoro ethylene and polyether-urethane. It is preferred that the surface activation is due to the presence of surface sulfonated fibers onto which is immobilized a hemocompatible molecule such as albumin. It is also preferred that those constructs comprise a bioactive agent selected from the group represented by antimicrobials, antiseptics, anesthetics, analgesics, wound healing agents, anti-inflammatory compounds, antiviral agents and growth promoters.

A clinically important aspect of this invention deals with a hemostatic, compliant, elastomeric, multicomponent, fibrous construct comprising non-woven nanometer and micrometer diameter fibers made from at least one polymer selected from the groups represented by synthetic absorbable/biodegradable heterochain polymers, synthetic water-soluble heterochain polymers, synthetic water-soluble homochain polymers, and polysaccharides or derivatives thereof, wherein the nanometer and micrometer diameter fibers are produced by electrostatic spinning of a solution of at least one absorbable polymer made from at least one monomer selected from the group represented by ε-caprolactone, dl-lactide, 1-lactide, glycolide, trimethylene carbonate, 1,5-dioxepan-2-one, p-dioxanone, and a substituted or unsubstituted morpholine-2-5-dione, wherein such construct is a part of the internal surface of a partially absorbable woven or knitted mesh for repairing defective walls as in abdominal wall, and urinary bladder wall wherein said mesh is made of monofilament or multifilament yarn made of at least one polymer selected from the group represented by polyethylene, polypropylene, poly(ethylene-co-polypropylene, polyether-ether ketone, polyethylene terephthalate, and poly(ethylene-co-tetrafluoro ethylene), and wherein the tissue-contacting surface is sulfonated and comprising at least one growth promoter.

Another segment of this invention deals with a hemostatic, compliant, elastomeric, multicomponent, fibrous construct comprising non-woven nanometer and micrometer diameter fibers made from at least one polymer selected from the groups represented by synthetic absorbable/biodegradable heterochain polymers, synthetic water-soluble heterochain polymers, synthetic water-soluble homochain polymers, and polysaccharides or derivatives thereof and wherein such a construct is a part of a composite fabric comprising chitosan fibers or derivatives thereof.

DETAILED DESCRIPTION OF PREFERRED EMBODIMENTS

Webster's New World Dictionary ($2^{nd}$ College Edition, 1970) defines hemostasis as (1) the stoppage of bleeding, and (2) the stoppage of the flow of blood in a vein or artery, as with a tourniquet. Meanwhile, the Webster's Medical Desk Dictionary (1986) defines hemostasis as (1) stoppage or sluggishness of blood flow, and (2) arrest of bleeding (as by a hemostatic agent). Hence, it is not surprising that inventors of the prior art have dealt with hemostasis as it relates to (1) the stoppage of bleeding of accidental wounds; (2) the arrest of bleeding during or after surgical procedures; and (3) pathologically induced blood clotting. Contrary to the limited perspective of the inventors of the prior art to hemostasis and consistent with recent understanding of the relevance of hemostasis to key and distinctly vital biological events associated with wound healing, tissue ingrowth about absorbable and non-absorbable prosthetic devices, and tissue engineering justified the need to explore means to modulating the hemostatic process to meet the specific requirements at different biological sites for optimum hemostasis and hence, optimum functional performance at said sites. Accordingly, this invention was intended to deal with (1) the technology of electrostatic spinning to produce nanometer and micrometer diameter fibers with exceptionally high surface area for maximized effect on blood flow and initiating the clotting cascade through contact activation; (2) production of at least one inherently compliant, elastic component of the fibrous construct through the use of segmented crystalline copolymers having triaxial or polyaxial chain configuration (i.e., three or many chain branches extending outward from a central atom); (3) control of the composition of electrostatically spun fiber precursors to provide constructs with controlled solubility and biodegradability and hence, modulated short- and long-term retention of mass and biologically relevant properties; (4) control of the surface charge of the electrostatically spun fibers to physicochemically modulate the hemostasis at will; and (5) judicious incorporation of bioactive agents to prevent infection, pain, and/or promote desirable biological events.

In concert with these general tenets, the present invention deals with a multicomponent and preferably bicomponent nano- or microfibrous construct produced by at least one absorbable, inherently compliant elastomeric polymer and second polymer that can be water-soluble or non-absorbable. With the proper selection of the constituent polymers, electro-spinning solvent, and electrospinning conditions, one can produce constructs that can be optimally suited for use at different biological sites to meet the specific requirements for optimum performance and/or restore the respective biological functions at said treated sites. This invention also deals with the formation of bicomponent nanofiber/microfibers having a core/sheath structure, wherein the core and sheath are based primarily on two physicochemically different polymers. The production of bicomponent nanofibers/microfibers can be achieved through controlling (1) the polymer molecular weight; (2) the type of spinning solvent and hence, the solvent-polymer interaction; (3) concentration of the individual polymers; and (4) the electrospinning parameters. To further maximize the effectiveness of certain fibrous constructs, at least one bioactive agent can be added to the spinning solution to meet the specific requirements at the treated biological site.

An illustrative example of the basic tenets of this invention is associated with the use of different agents at sites where hemostasis is paramount to wound healing. It is well recognized that the process of wound healing is one that is complex and can be compromised by a number of contributing factors. One such factor is infection of the wound. Although many types of wound dressings are currently used in the management of wounds caused by burns, split skin graft donor sites, pressure sores, and diabetic ulcers, infection under the wound dressing remains a formidable problem. Bacterial infection of wounds can significantly compromise the healing process and in some cases, prevent wound healing. One of the methods for treating infections is through the use of antibiotics. Although antibiotics have been proven to be very useful against wound infections, it also has been reported that their use can be associated with complications such as renal and liver toxicity and the emergence of drug-resistant bacteria. Patients with chronic wound injuries are often treated with systemic antibiotics in an attempt to decrease the bacterial load present in the wound. However, it is known that despite the abundant blood supply present in granulating tissue, systemic administration often does not produce appreciable levels of antibiotics in granulating tissue. Further, ischemic wounds with little granulation tissue also have poor penetration by systemically administered antibiotics. Therefore, topical administration has proven to be an effective approach. In the ideal case, the antibiotic is used in appropriate amounts at the site of the infection and for the duration of the infection. For this, a fibrous construct that is (1) compliant so as to insure biomechanical compatibility with a soft tissue biological site; (2) elastomeric to insure the ability to conform to accommodate swelling at the wound site, which often occurs as a result of transient and persistent tissue reaction; and (3) absorbable to avoid undesirable secondary events associated with non-absorbable, permanent implants.

Another illustrative example of the tenets of this invention is associated with the use of the hemostatic, compliant, elastomeric, multicomponent, fibrous construct as an absorbable wrap or a pledget to aid in completing a less invasive vascular anastomosis using sutures, staples, and/or tissue adhesives. When a combination of fewer suture stitches and absorbable tissue adhesive are used to achieve vascular anastomosis, the absorbable fibrous construct, subject of this invention, will function as a substrate for even distribution of the tissue adhesive about the anastomotic site and form a bridge between the suture and tissue adhesive leading to more mechanically secure anastomosis.

Another illustrative example of the tenets of this invention deals with the absorbable elastomeric, compliant, fibrous construct as a microporous template for effective application of tissue adhesive in repairing wounds or lacerations of exceptionally soft tissue as in the lung, liver, and pancreas.

Another illustrative example of the tenets of this invention is the use of a partially absorbable elastomeric, compliant, fibrous construct as a component of a vascular graft wherein the lumen of the graft is made of a non-absorbable woven or knitted yarn as for example, polypropylene, that is preferably treated to prevent hemostasis at the blood contacting surface while the outer wall of the graft is made primarily of an absorbable, compliant, elastomeric microfiber which can preferably contain a growth promoter to allow early and continued tissue ingrowth into the outer wall of the graft; this is to insure initial and long-term stability at the treated site.

This invention deals in general with a hemostatic, compliant, elastomeric, multicomponent, fibrous construct comprising non-woven nanometer and micrometer diameter fibers made from at least one polymer selected from the groups represented by synthetic absorbable/biodegradable heterochain polymers, synthetic water-soluble heterochain polymers, synthetic water-soluble homochain polymers, and polysaccharides or derivatives thereof. Another general aspect of this invention deals with a hemostatic, compliant, elastomeric, fibrous construct comprising a non-woven material comprising fibers having a diameter in the range of from about 50 nm to about 10 μm, the fibers having a core/sheath configuration and made from a synthetic absorbable/biodegradable polymer and at least one further polymer selected from a synthetic water-soluble polymer and another synthetic absorbable/biodegradable polymer.

A specific aspect of this invention deals with a hemostatic, compliant, elastomeric, multicomponent, fibrous construct comprising non-woven nanometer and micrometer diameter fibers made from at least one polymer selected from the groups represented by synthetic absorbable/biodegradable heterochain polymers, synthetic water-soluble heterochain polymers, synthetic water-soluble homochain polymers, and polysaccharides or derivatives thereof, wherein the nanometer and micrometer diameter fibers are produced by electrostatic spinning of a solution of at least one absorbable polymer made from at least one monomer selected from the group represented by ϵ-caprolactone, dl-lactide, l-lactide, glycolide, trimethylene carbonate, 1,5-dioxepan-2-one, p-dioxanone, and a substituted or unsubstituted morpholine-2-5-dione.

Another specific aspect of this invention deals with a hemostatic, compliant, elastomeric, multicomponent, fibrous construct comprising non-woven nanometer and micrometer diameter fibers made from at least one polymer selected from the groups represented by synthetic absorbable/biodegradable heterochain polymers, synthetic water-soluble heterochain polymers, synthetic water-soluble homochain polymers, and polysaccharides or derivatives thereof, wherein the nanometer and micrometer diameter fibers are produced by electrostatic spinning of a solution comprising an absorbable/biodegradable polymer made from at least one monomer selected from the group represented by ϵ-caprolactone, dl-lactide, l-lactide, glycolide, trimethylene carbonate, 1,5-dioxepan-2-one, p-dioxanone, a substituted or unsubstituted morpholine-2-5-dione, and a synthetic, water-soluble polymer selected from the group represented by polyethylene oxide, polyethylene glycol, block copolymer of ethylene and propylene glycol, polyhydroxyethyl methacrylate, poly-N-vinyl pyrrolidone and polyethylene glycol interlinked by an ester or urethane-containing interlink, wherein the absorbable/biodegradable and water-soluble constituents of the spinning solution result in biocomponent fibers having a core and sheath component derived primarily from the absorbable/biodegradable and water-soluble polymer, respectively, and preferably the water-soluble polymer is polyethylene glycol and the absorbable/biodegradable polymer is a triaxial segmented copolyester based on at least two monomers selected from the group represented by ϵ-caprolactone, dl-lactide, l-lactide, glycolide, trimethylene carbonate, 1,5-dioxepan-2-one, p-dioxanone, and a substituted or unsubstituted morpholine-2-5-dione.

Further, the present invention is directed to a hemostatic, compliant, elastomeric, fibrous construct as set forth in claim 3 wherein the water-soluble polymer is selected from the group consisting of polyethylene oxide, polyethylene glycol, and a block copolymer of ethylene and propylene glycols, and wherein the absorbable/biodegradable polymer further comprises pendant carboxyl groups ionically conjugated with a basic compound selected from the group consisting of lysine, arginine, a basic oligopeptide, antiseptic agents, anesthetic agents, analgesic agents, antimicrobial agents, anti-inflammatory agents, antiviral agents and growth promoters.

Another specific aspect of this invention deals with a hemostatic, compliant, elastomeric, multicomponent, fibrous construct comprising non-woven nanometer and micrometer diameter fibers made from at least one polymer selected from the groups represented by synthetic absorbable/biodegradable heterochain polymers, synthetic water-soluble heterochain polymers, synthetic water-soluble homochain polymers, and polysaccharides or derivatives thereof, wherein the nanometer and micrometer diameter fibers are produced by electrostatic spinning of a solution comprising an absorbable/biodegradable polymer made from at least one monomer selected from the group represented by ϵ-caprolactone, dl-lactide, l-lactide, glycolide, trimethylene carbonate, 1,5-dioxepan-2-one, p-dioxanone, a substituted or unsubstituted morpholine-2-5-dione, and a synthetic, water-soluble polymer selected from the group represented by polyethylene oxide, polyethylene glycol, block copolymer of ethylene and propylene glycol, polyhydroxyethyl methacrylate, poly-N-vinyl pyrrolidone and polyethylene glycol interlinked by an ester or urethane-containing interlink, and wherein the absorbable/biodegradable and water-soluble constituents of the spinning solution result in bicomponent fibers having a core and sheath component derived primarily from the water-soluble and absorbable/biodegradable polymer, respectively.

Another aspect of the invention pertains to hemostatic, compliant, elastomeric, multicomponent, fibrous construct comprising non-woven nanometer and micrometer diameter fibers made from at least one polymer selected from the groups represented by synthetic absorbable/biodegradable heterochain polymers, synthetic water-soluble heterochain polymers, synthetic water-soluble homochain polymers, and polysaccharides or derivatives thereof, wherein the nanometer and micrometer diameter fibers are produced by electrostatic spinning of a solution comprising an absorbable/biodegradable polymer made from at least one monomer selected from the group represented by ϵ-caprolactone, dl-lactide, l-lactide, glycolide, trimethylene carbonate, 1,5-dioxepan-2-one, p-dioxanone, a substituted or unsubstituted morpholine-2-5-dione, and a synthetic, water-soluble polymer selected from the group represented by polyethylene oxide, polyethylene glycol, block copolymer of ethylene and propylene glycol, polyhydroxyethyl methacrylate, poly-N-vinyl pyrrolidone and polyethylene glycol interlinked by an ester or urethane-containing interlink, wherein the absorbable/biodegradable and water-soluble constituents of the spinning solution result in bicomponent fibers having a core and sheath component derived primarily from the absorbable/biodegradable and water-soluble polymer, respectively, and preferably the water-soluble polymer is a poly-N-vinyl pyrrolidone and the absorbable/biodegradable polymer is a triaxial segmented copolyester based on at least two monomers selected from the group represented by ϵ-caprolactone, dl-lactide, l-lactide, glycolide, trimethylene carbonate, 1,5-dioxepan-2-one, p-dioxanone, and a substituted or unsubstituted morpholine-2-5-dione.

Another aspect of this invention deals with use of said fibrous construct, the subject of this invention as (1) a lint-free, absorbent surgical pad; (2) an adjuvant in surgical procedures selected from the group represented by vascular anastomosis with sutures or tissue adhesives, intestinal anastomosis with sutures, staples or tissue adhesives, vascular repair entailing synthetic vascular graft using sutures or tissue adhesives, and structural repair of a biological conduit entailing synthetic prosthesis using sutures, staples, or tissue adhesives; and (3) a pledget for repairing soft tissue as in liver, kidney, pancreas, and lung using sutures, clips, or tissue adhesives. It is preferred that those constructs comprise a bioactive agent selected from the group represented by antimicrobials, antiseptics, anesthetics, analgesics, wound healing agents, anti-inflammatory compounds, antiviral agents and growth promoters.

A key aspect of the invention deals with a fibrous construct, subject of this invention, as a cover of a prosthetic device to aid/promote tissue ingrowth and mechanical stabilization of said prosthesis, wherein the prosthesis is selected from the group represented by endovascular grafts, perivascular wraps, vascular patches, endovascular stents, and similar stents for repairing biological conduits or restoring their function, endosteal implants, orthopedic implants, and implants for soft and hard tissue engineering. It is preferred that those constructs comprise a bioactive agent selected from the group represented by antimicrobials, antiseptics, anesthetics, analgesics, wound healing agents, anti-inflammatory compounds, antiviral agents and growth promoters.

Another key aspect of this invention pertains to a hemostatic, compliant, elastomeric, multicomponent, fibrous construct comprising non-woven nanometer and micrometer diameter fibers made from at least one polymer selected from the groups represented by synthetic absorbable/biodegradable heterochain polymers, synthetic water-soluble heterochain polymers, synthetic water-soluble homochain polymers, and polysaccharides or derivatives thereof, wherein said construct comprises a bioactive agent selected from the group represented by antimicrobials, antiseptics, anesthetics, analgesics, wound healing, anti-inflammatory, growth promoters, and antiviral agents.

A specific aspect of this invention deals with a hemostatic, compliant, elastomeric, multicomponent, fibrous construct comprising non-woven nanometer and micrometer diameter fibers made from at least one polymer selected from the groups represented by synthetic absorbable/biodegradable heterochain polymers, synthetic water-soluble heterochain polymers, synthetic water-soluble homochain polymers, and polysaccharides or derivatives thereof, wherein the nanometer and micrometer diameter fibers are produced by electrostatic spinning of a solution comprising an absorbable/biodegradable polymer made from at least one monomer selected from the group represented by ϵ-caprolactone, dl-lactide, l-lactide, glycolide, trimethylene carbonate, 1,5-dioxepan-2-one, p-dioxanone, a substituted or unsubstituted morpholine-2-5-dione, and a synthetic, water-soluble polymer selected from the group represented by polyethylene oxide, polyethylene glycol, block copolymer of ethylene and propylene glycol, polyhydroxyethyl methacrylate, poly-N-vinyl pyrrolidone and polyethylene glycol interlinked by an ester or urethane-containing interlink, and preferably the water-soluble component is a polyvinyl pyrrolidone complexed with iodine.

Another specific aspect of the invention pertains to a hemostatic, compliant, elastomeric, multicomponent, fibrous construct comprising non-woven nanometer and micrometer diameter fibers made from at least one polymer selected from the groups represented by synthetic absorbable/biodegradable heterochain polymers, synthetic water-soluble heterochain polymers, synthetic water-soluble homochain polymers, and polysaccharides or derivatives thereof, wherein the nanometer and micrometer diameter fibers are produced by electrostatic spinning of a solution comprising an absorbable/biodegradable polymer made from at least one monomer selected from the group represented by ϵ-caprolactone, dl-lactide, l-lactide, glycolide, trimethylene carbonate, 1,5-dioxepan-2-one, p-dioxanone, a substituted or unsubstituted morpholine-2-5-dione, and a synthetic, water-soluble polymer selected from the group represented by polyethylene oxide, polyethylene glycol, block copolymer of ethylene and propylene glycol, polyhydroxyethyl methacrylate, poly-N-vinyl pyrrolidone and polyethylene glycol interlinked by an ester or urethane-containing interlink, and preferably the water-soluble component is polyethylene glycol or block copolymer of ethylene and propylene glycol comprising a conjugate of carboxyl-bearing absorbable copolyester and a basic compound selected from the group represented by lysine, arginine, a basic oligopeptide, antiseptic agents, anesthetic agents, analgesic agents, antimicrobial agents, anti-inflammatory agents, antiviral agents and growth promoters.

An important aspect of this invention deals with a hemostatic, compliant, elastomeric, multicomponent, fibrous construct comprising non-woven nanometer and micrometer diameter fibers made from at least one polymer selected from the groups represented by synthetic absorbable/biodegradable heterochain polymers, synthetic water-soluble heterochain polymers, synthetic water-soluble homochain polymers, and polysaccharides or derivatives thereof, wherein the nanometer and micrometer fibers are produced by electrostatic spinning of a solution of at least one polymer that absorbs in less than 120 days and at least one additional polymer that absorbs after more than 120 days wherein each of these polymers is made from at lest one monomer selected for the group represented by ϵ-caprolactone, dl-lactide, l-lactide, glycolide, trimethylene carbonate, 1,5-dioxepan-2-one, p-dioxanone, and a substituted or unsubstituted morpholine-2-5-dione, and preferably at least one of the polymers comprises a linear chain absorbable copolyester and an additional polymer comprising an absorbable copolyester comprising polyaxial copolyester chains.

A key segment of this invention pertains to a hemostatic, compliant, elastomeric, multicomponent, fibrous construct comprising non-woven nanometer and micrometer diameter fibers made from at least one polymer selected from the groups represented by synthetic absorbable/biodegradable heterochain polymers, synthetic water-soluble heterochain polymers, synthetic water-soluble homochain polymers, and polysaccharides or derivatives thereof, wherein the nanometer and micrometer diameter fibers are produced by electrostatic spinning of a solution of at least one absorbable polymer made from at least one monomer selected from the group represented by ϵ-caprolactone, dl-lactide, l-lactide, glycolide, trimethylene carbonate, 1,5-dioxepan-2-one, p-dioxanone, and a substituted or unsubstituted morpholine-2-5-dione, wherein such construct is part of the external wall of a vascular graft having a surface-activated, non-absorbable lumen comprising knitted or woven monofilament or multifilament yarn made of at least one polymer selected from the group represented by polyethylene, polypropylene, poly(ethylene-co-polypropylene, polyether-ether ketone, polyethylene terephthalate, poly(ethylene-co-tetrafluoro ethylene and polyether-urethane. It is preferred that the surface activation is due to the presence of surface sulfonated fibers onto which is immobilized a hemocompatible molecule such as albumin. It is also preferred that those constructs comprise a bioactive agent selected from the group represented by antimicrobials, antiseptics, anesthetics, analgesics, wound healing agents, anti-inflammatory compounds, antiviral agents and growth promoters.

A clinically important aspect of this invention deals with a hemostatic, compliant, elastomeric, multicomponent, fibrous construct comprising non-woven nanometer and micrometer diameter fibers made from at least one polymer selected from the groups represented by synthetic absorbable/biodegradable heterochain polymers, synthetic water-soluble heterochain polymers, synthetic water-soluble homochain polymers, and polysaccharides or derivatives thereof, wherein the nanometer and micrometer diameter fibers are produced by electrostatic spinning of a solution of at least one absorbable polymer made from at least one monomer selected from the group represented by ϵ-caprolactone, dl-lactide, l-lactide, glycolide, trimethylene carbonate, 1,5-dioxepan-2-one, p-dioxanone, and a substituted or unsubstituted morpholine-2-5-dione, wherein such construct is a part of the internal surface of a partially absorbable woven or knitted mesh for repairing defective walls as in abdominal wall, and urinary bladder wall wherein said mesh is made of monofilament or multifilament yarn made of at least one polymer selected from the group represented by polyethylene, polypropylene, poly(ethylene-co-polypropylene, polyether-ether ketone, polyethylene terephthalate, and poly(ethylene-co-tetrafluoro ethylene), and wherein the tissue-contacting surface is sulfonated and comprising at least one growth promoter.

Another segment of this invention deals with a hemostatic, compliant, elastomeric, multicomponent, fibrous construct comprising non-woven nanometer and micrometer diameter fibers made from at least one polymer selected from the groups represented by synthetic absorbable/biodegradable heterochain polymers, synthetic water-soluble heterochain polymers, synthetic water-soluble homochain polymers, and polysaccharides or derivatives thereof and wherein such a construct is a part of a composite fabric comprising chitosan fibers or derivatives thereof.

Additional illustrations of the present invention are provided in the examples given below.

Example 1

Synthesis of a Caprolactone/Trimethylene Copolymer and Use as Triaxial Initiator for End-Grafting l-Lactide/ε-Caprolactone to Produce Crystalline Segmented Triaxial Copolymer (PAX)

Following a similar method to those described in U.S. Pat. No. 6,462,169, a triaxial polymeric copolymer was made from 50/50 (molar) caprolactone and trimethylene carbonate (TMC) and then end-grafted with 90/10 (molar) l-lactide/TMC. Accordingly, the polymeric initiator was prepared by ring opening polymerization of ε-caprolactone (0.25 mole) and TMC (0.25 mole) in the presence of stannous octanoate as a catalyst (at a monomer/catalyst ratio of 15,000) and triethanolamine as the initiator (at a monomer to initiator ratio of 300). The polymerization was achieved by heating at 180° C. for 3 hours. The resulting product was cooled below 150° C. and then mixed under nitrogen atmosphere with l-lactide (0.45 mole) and ε-caprolactone (0.05 mole). The system was stirred while heating to 190-200° C. to achieve a uniform melt. The temperature was then lowered to 140° C. and the reaction was continued without stirring for 24 hours. The polymer was isolated, ground, dried, and heated under reduced pressure to remove unreacted monomer. The polymer was characterized by IR and NMR (for identity), GPC ($M_w$=130 kDa), thermal transition ($T_m$=155° C.), and inherent viscosity (I.V.) in chloroform (I.V.=1.0 dL/g).

Example 2

Preparation of Poly(ε-Caprolactone)

Caprolactone (1 mole) was polymerized under similar conditions to those used in Example 1 using stannous octanoate as a catalyst (monomer/catalyst molar ratio=10,000) and 1,3-propanediol as the initiator (monomer/initiator molar ratio=600). The polymerization was conducted at 180° C. for 4 hours. The polymer was isolated, purified, and characterized as described for PAX in Example 1. The polymer revealed a $T_m$=65° C., $M_w$=130 kDa, and I.V.=1.3 dL/g.

Example 3

Preparation of Urethane-Interlinked Polyethylene Glycol 8000 (PEG-8000-I)

Predried PEG-8000 (0.01 mole) was mixed in a mechanically stirred reactor at 70° C. with diisocyanatohexane (0.01 mole) until uniform melt is attained. The temperature of the reaction mixture was raised to 130° C. while stirring over 1.5 hours. The reaction was continued for an additional 3 hours at 140° C. The product was isolated in a dry atmosphere as a white solid. The produce was analyzed for thermal transition (DSC, $T_m$=62° C.), molecular weight (GPC, $M_w$=30 kDa), and identity/composition (NMR and IR).

Example 4

General protocol for the Electrostatic Spinning of Polymer Solutions and Characterization of Resulting Non-Woven Nano-/Microfibrous Fabric Using standard equipment for electrostatic spinning of a solution of one or more polymer(s) in one or more solvent(s) (e.g., chloroform, $CHCl_3$ and/or dichloromethane DCM) is electrospun using (1) 15 to 35 percent (w/v) solution depending on the molecular weight of the polymer(s); (2) a voltage differential of 15-20 KV depending on the sought fiber diameter; (3) a tip-to-collection distance (distance between extruder and collection unit) of 7-10" depending on the desired diameter and solvent used; and (4) a solution delivery rate of 0.1 to 0.3 mL/min. depending on the solvent volatility. In most cases, heating of the surrounding environment was not needed. The resulting non-woven fabric is collected on a metallic cylinder (e.g., different diameter stainless steel cylinder) capable of controllable radial and axial motion. The electrospun construct, at a thickness of 0.1 to 2 mm, is collected for subsequent characterization for (1) bulk composition using NMR and IR; (2) surface composition using electron spectroscopy for chemical analysis (ESCA); (3) fiber diameter and fabric uniformity (SEM); (4) molecular weight (GPC, inherent viscosity); (5) thermal transitions associated with crystalline melting, glass transition melting, or heat of fusion; (6) burst testing/radial deformation (in-house modified cone penetration test); (7) tensile properties using a Universal MiniBionix tensile tester Model 858; (8) oxygen and water vapor permeation (standard ASTM protocol); (9) surface free energy (static and dynamic contact angle measurements); and (10) partial water solubility and associated change in morphology and mass (SEM and mass loss).

Example 5

Electrostatic Co-Spinning of a Mixed Solution of PAX and Polycaprolactone (PCL) and Comparison with a PCL Microfabric Control A 20% solution of equal weights of PAX and PCL (from Examples 1 and 2) in dichloromethane was spun into a 0.2 mm thick nano-/microfibrous construct. The resulting fabric was characterized for morphology (SEM) and tensile properties. Comparison of the bicomponent PAX/PCL constructs with a polycaprolactone control, produced using identical conditions, revealed that the former bicomponent fabric is more compliant and elastomeric with minor differences in fiber dimension as compared to the single-component control. The sheath of the bicomponent fiber was found to contain PAX as the major constituent.

Example 6

Electrostatic Co-Spinning of a Mixed Solution of PAX and Polyethylene Glycol 1000 (PEG-1000) and Comparison with PAX Fabric Control A 15% solution of a 99/1 PAX/PEG-1000 mixture in 50/50 chloroform/dichloromethane ($CHCl_3$/DCM) was electrospun into 0.2 mm thick non-woven fabric. Using pertinent analytical techniques (as in Example 4) the PAX/PEG fabric was shown to be more wettable than the PAX control.

Example 7

Electrostatic Co-Spinning of a Mixed Solution of PAX and Polyethylene Oxide (PEO-100) and Comparison with a PAX Control A 20% solution of a mixture containing equal amounts of PAX and PEO-100 (molecular weight=100 kDa) in dichloromethane was spun to a 0.2 mm thick microfibrous non-woven construct, which was characterized using pertinent analytical techniques (as in Example 4). The PAX/PEO-100 was shown to comprise microfibers with a PEO-100-rich water soluble sheath. The preponderance of polyethylene oxide on the surface was verified by ESCA and fractional dissolution of the sheath in deionized water. The PAX/PEO-100 fabric was shown to be more hydrophilic and wettable as compared to the PAX control.

Example 8

Electrostatic Co-Spinning of a Mixed Solution of PAX and Urethane-Interlinked PEG-8000 and Comparison with a PAX Control This was conducted as described in Example 7 with the exception of substituting PEO-100 with interlinked PEG-8000 (PEG-8000-I) from Example 3. Results of pertinent analytical protocols (as described in Example 7) indicate that (1) constituent fibers are bicomponent in nature having a PEG-8000-I present in the sheath; and (2) the surface is more hydrophilic and wettable as compared with the PAX control.

Example 9

Electrostatic Co-Spinning of PAX and Polyvinylpyrrolidone (PVP) and Comparison with a PAX Control This was conducted as described in Example 7 with the exception of (1) substituting PEO-100 with PVP having a molecular weight of 55 kDa; (2) using a 33/67 DCM/CHCl$_3$ mixture as a solvent; and (3) a mixture of 43/57 PAX/PVP. Using pertinent analytical methods indicated that the fabric made of PAX/PVP (1) is more wettable and hydrophilic than the PAX control; (2) the constituent fibers are bicomponent with a PAX-rich sheath; and (3) the fabric density can be reduced by dissolving the PVP-rich core.

Example 10

Electrostatic Co-Spinning of PAX and Polyvinylpyrrolidone (PVP) and Comparison with a PAX Control This was conducted as described in Example 9 with the exception of (1) using 40% DCM and 60% CHCl$_3$ as a solvent; and (2) a mixture of 20/80 PAX/PVP. Using pertinent analytical methods it was indicated that the fabric made of PAX/PVP (1) is more wettable and hydrophilic than the PAX control; (2) the constituent fibers are bicomponent with a PVP-rich sheath and a PAX-rich core; and (3) the fiber diameter and fabric density can be reduced by dissolving the PVP-rich sheath.

Example 11

Electrostatic Co-Spinning of PAX with PVP/Iodine Complex and Comparison with a PAX Control This was conducted as described in Example 10 with the exception of complexing the PVP with 1% iodine in CHCl$_3$ prior to mixing with the PAX solution. With the exception of being yellowish in color, the properties of the microfibrous construct were very similar to those of Example 10.

Example 12

Incorporation of Trichlosan Sodium in a PCL/PAX Microfabric

The PCL/PAX microfabric from Example 5 was treated with a 2% solution of trichlosan sodium in 2-propanol following a similar protocol to that disclosed in U.S. Pat. No. 6,551,610. The treated specimen was dried and shown to release about 7% of the incorporated drug in 3 days when incubated in deionized water at 37° C.

Example 13

Surface Activation and Testing of the Microfabric

In a typical experiment, a microfabric specimen was incubated in 1% solution of arginine for 5 to 30 minutes at room temperature. The treated, non-woven fabric was then rinsed with deionized water and dried to a constant weight. The dried fabric was tested for (1) wettability (static and dynamic contact angle); (2) presence of bound nitrogen (ESCA and elemental analysis); (3) tensile and burse strength; and (4) in vitro blood clotting.

Example 14

Evaluation of the Relative Hemostatic Properties of Nano-/Microfibrous Non-Woven Fabric In a typical case, a 20×20×0.2 mm fabric specimen was tested for its ability to arrest bleeding in a standard liver laceration and punctured vena cava of an anesthetized rabbit and/or rat model. In general, the hemostatic property was shown to substantially improve by increasing the composite fabric wettability, decrease in diameter of constituent fibers, and/or positive surface charge as compared with a PCL or PAX control. All examined specimens showed superior hemostatic properties as compared to commercial specimens of chitosan non-woven fabric, chitosan foam, and cotton gauze.

Preferred embodiments of the invention have been described using specific terms and devices. The words and terms used are for illustrative purposes only. The words and terms are words and terms of description, rather than of limitation. It is to be understood that changes and variations may be made by those of ordinary skill art without departing from the spirit or scope of the invention, which is set forth in the following claims. In addition it should be understood that aspects of the various embodiments may be interchanged in whole or in part. Therefore, the spirit and scope of the appended claims should not be limited to descriptions and examples herein.

What is claimed is:

1. A hemostatic, compliant, elastomeric, fibrous construct comprising a non-woven material comprising fibers produced by electrostatic spinning of a solution and having a diameter in the range of from about 50 nm to about 10 μm, the fibers having a core/sheath configuration and made from at least one synthetic absorbable polymer and at least one further polymer comprising a synthetic water-soluble polymer, the solution comprising an absorbable polymer made from at least one monomer selected from the group consisting of ε-caprolactone, dl-lactide, l-lactide, glycolide, trimethylene carbonate, 1,5-dioxepan-2-one, p-dioxanone, and a substituted or unsubstituted morpholine-2-5-dione, and a synthetic, water-soluble polymer consisting of polyethylene glycol interlinked by an ester or urethane interlink.

2. A hemostatic, compliant, elastomeric, fibrous construct as set forth in claim 1 wherein the absorbable and water-soluble constituents of the spinning solution form bicomponent fibers having a core component and a sheath component, the core component comprising the absorbable polymer and the sheath component comprising the water-soluble polymer.

3. A hemostatic, compliant, elastomeric, fibrous construct as set forth in claim 2 wherein the absorbable polymer comprises a triaxial segmented copolyester formed from at least two monomers selected from the group consisting of ε-caprolactone, dl-lactide, l-lactide, glycolide, trimethylene carbonate, 1,5-dioxepan-2-one, p-dioxanone, and a substituted or unsubstituted morpholine-2-5-dione.

4. A method of making a hemostatic, compliant, elastomeric, fibrous construct having a diameter in the range of from about 50 nm to about 10 μm, the fibers having a core/sheath configuration comprising electrostatic spinning of a solution comprising i) an absorbable polymer made from at least one monomer selected from the group consisting of ε-caprolactone, dl-lactide, l-lactide, glycolide, trimethylene carbonate, 1,5-dioxepan-2-one, p-dioxanone, and a substituted or unsubstituted morpholine-2-5-dione, and ii) a polymer consisting of polyethylene glycol interlinked by an ester or urethane interlink.

5. The method of claim 4 wherein the absorbable polymer comprises a triaxial segmented copolyester formed from at least two monomers selected from the group consisting of ε-caprolactone, dl-lactide, l-lactide, glycolide, trimethylene carbonate, 1,5-dioxepan-2-one, p-dioxanone, and a substituted or unsubstituted morpholine-2-5-dione.

6. The method of claim 4 wherein the ester or urethane interlink is a diisocyanate interlink.

7. A hemostatic, compliant, elastomeric, fibrous construct as set forth in claim 1 wherein the ester or urethane interlink is a diisocyanate interlink.

8. A hemostatic, compliant, elastomeric, fibrous construct as set forth in claim 2 wherein the ester or urethane interlink is a diisocyanate interlink.

9. A hemostatic, compliant, elastomeric, fibrous construct as set forth in claim 3 wherein the ester or urethane interlink is a diisocyanate interlink.

* * * * *